United States Patent [19]

Logé et al.

[11] 4,212,640

[45] Jul. 15, 1980

[54] DENTAL HANDPIECE

[75] Inventors: Hans Logé, Biberach an der Riss; Eugen Eibofner; Bernhard Kuhn, both of Biberach; Heinrich Reich, Hochdorf, all of Fed. Rep. of Germany

[73] Assignee: Kaltenbach & Voigt GmbH & Co., Biberach an der Riss, Fed. Rep. of Germany

[21] Appl. No.: 854,015

[22] Filed: Nov. 22, 1977

[30] Foreign Application Priority Data

Nov. 25, 1976 [DE] Fed. Rep. of Germany ....... 2653588

[51] Int. Cl.² .............................................. A61C 1/10
[52] U.S. Cl. ..................................................... 433/82
[58] Field of Search ................ 32/28, 27, 26, DIG. 1; 433/82

[56] References Cited

U.S. PATENT DOCUMENTS

| 276,912 | 5/1883 | Starr | 32/26 |
|---|---|---|---|
| 1,747,947 | 2/1930 | Pannwitz | 32/26 |
| 2,937,444 | 5/1960 | Kern | 32/DIG. 1 |
| 3,298,701 | 1/1967 | Borden | 32/26 |
| 3,936,940 | 2/1976 | Loge | 32/26 |
| 4,007,529 | 2/1977 | Fleer | 32/27 |

FOREIGN PATENT DOCUMENTS

| 1260078 | 2/1968 | Fed. Rep. of Germany | 32/27 |
|---|---|---|---|
| 2311496 | 9/1974 | Fed. Rep. of Germany | 32/27 |
| 998442 | 7/1965 | United Kingdom | 32/DIG. 1 |

Primary Examiner—Louis G. Mancene
Assistant Examiner—John J. Wilson
Attorney, Agent, or Firm—Haseltine, Lake & Waters

[57] ABSTRACT

A dental handpiece having a sleeve, an axial drive shaft in the sleeve for driving a dental instrument at one end of the handpiece, a first coolant supply line in the handpiece, a second coolant supply line extending axially towards the dental instrument, and a coolant duct in the wall of the sleeve which intercommunicates the first and second coolant lines. The coolant duct extends rectilinearly and generally radially between an inner end which faces the interior of the sleeve and which communicates with the first coolant line, and an outer end which communicates with and is releasably connected to the second line at a location in the wall of the sleeve and which permits manipulation externally of the handpiece for releasing and connecting the duct and the second line.

27 Claims, 26 Drawing Figures

U.S. Patent   Jul. 15, 1980   Sheet 1 of 8   4,212,640
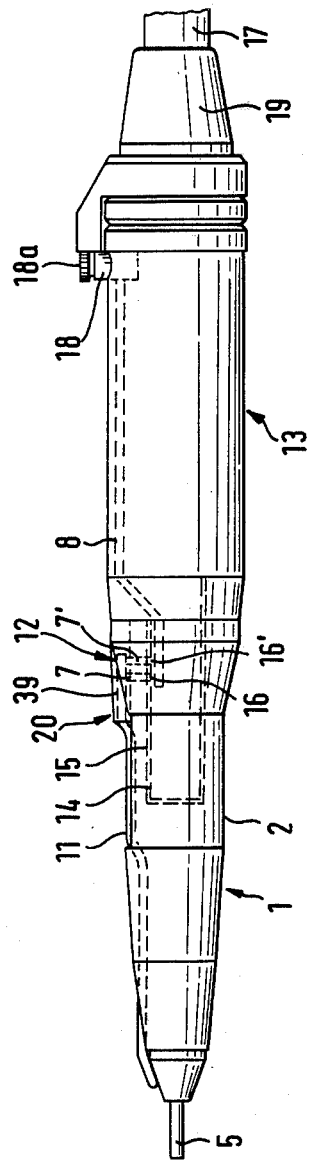
Fig.1
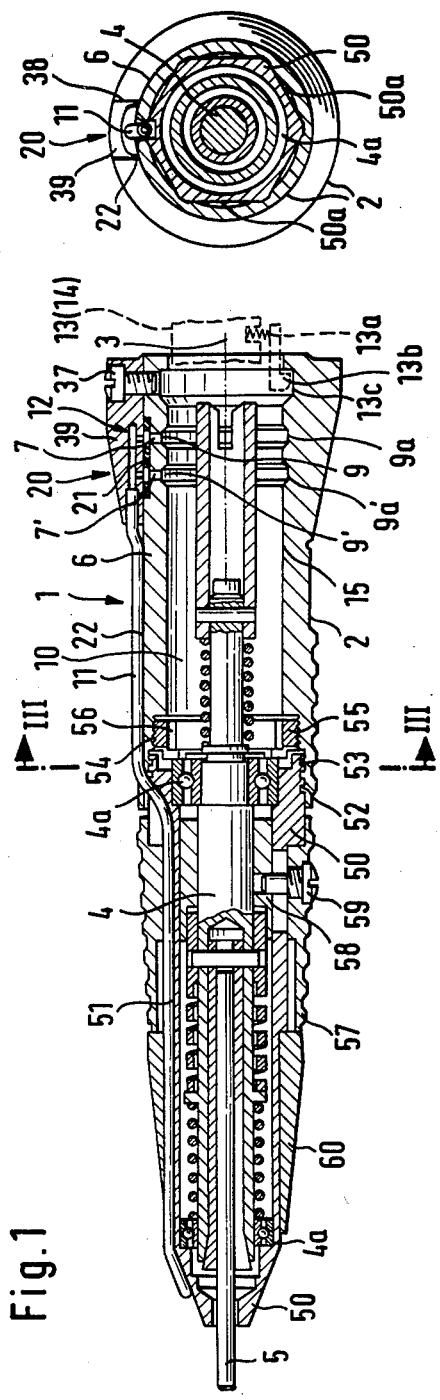
Fig.2
Fig.3

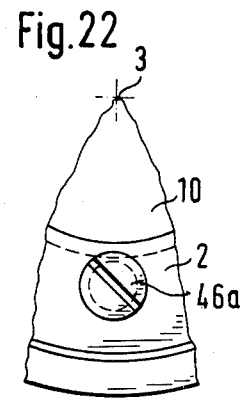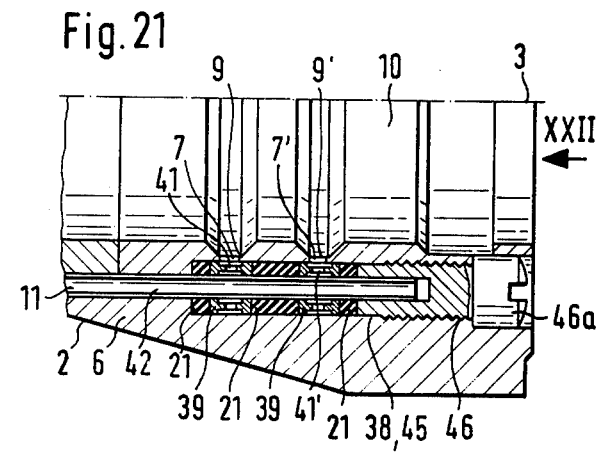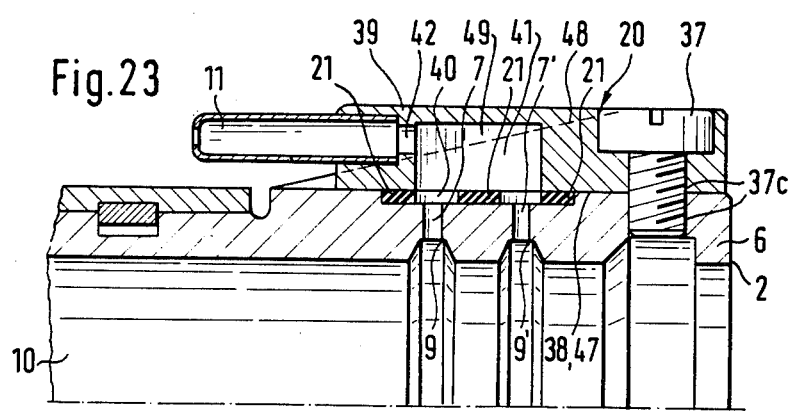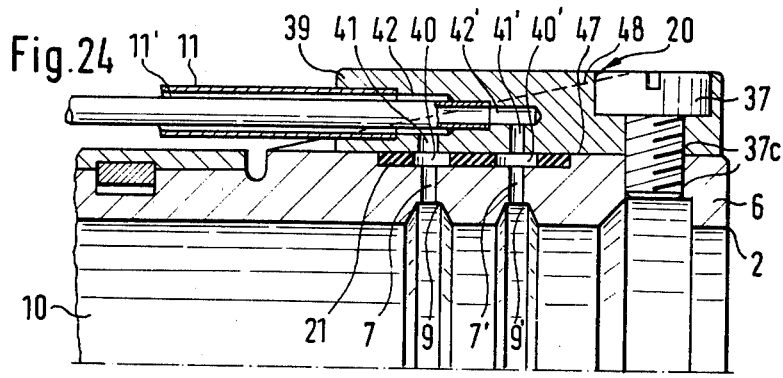

DENTAL HANDPIECE

This invention relates to a dental handpiece, comprising a drive shaft which is mounted in a handpiece sleeve and related to the handpiece sleeve extends axially, for the drive of a tooth-treatment implement connected with the drive shaft at a handpiece end, there being arranged in the walls of the handpiece sleeve a coolant duct the inlet aperture of which, connected with a coolant line, faces the handpiece interior, and which is releasably connected to a location accessible from the exterior, with a coolant line section extending substantially axially, in the zone of the tooth treatment implement. As coolant, there may be for example pressure air, water or a spray formed by an air-water mixture.

The arrangement of the coolant duct provided in the walls of the handpiece sleeve in such manner that its inlet aperture faces the handpiece interior has the advantage that on the one hand the inlet aperture is protected, also in the condition when released from the coolant line, against penetration of dirt or the like and on the other hand that the coolant line serving for coolant feed is located at the point of transition into the coolant duct in the handpiece interior. In this manner, the dentist grasping the handpiece in the zone of this transition location from the exterior is not hindered by the coolant line. Such hindering would occur if the coolant line were to extend externally or to be arranged in a thickened portion of the handpiece sleeve.

Such a dental handpiece is known from FIG. 1 of German Offenlegungsschrift No. 23 34 448. In the case of this known handpiece, the inlet aperture facing the handpiece interior of the coolant duct arranged in the walls of the handpiece sleeve debouches into an annular duct provided at the inner side of the walls of the handpiece sleeve. From the inlet aperture, the coolant duct extends obliquely outwardly and forwardly, i.e. to the tool-side end of the handpiece sleeve, until it emerges out of the walls of the handpiece sleeve. Directly after emergence out of the walls, the coolant duct is transferred by means of a curvature into a substantially axial extent, ending shortly before the curvature. With this end, the coolant line section extending to the zone of the tooth-treatment implement is releasably connected.

In consequence of the small diameter of the coolant duct of approximately 0.5 to 1 mm, there may readily result clogging due to contaminants contained in the coolant, whereby cleaning of the coolant duct becomes necessary. Such cleaning is, however, made difficult or even impossible due to the said curvature of the coolant duct. This is in particular very disadvantageous if the portion of the coolant duct having the curvature is—as is mostly the case—secured to the walls of the handpiece sleeve, because then it is necessary to replace the entire handpiece sleeve.

Known from German Offenlegungsschrift No. 24 31 472 is a dental handpiece in the case of which there is no coolant duct in the walls of the handpiece sleeve and consequently also no curvature of such a coolant duct. This known handpiece has, on the contrary, a coolant line section extending along at the outer side of the walls of the handpiece sleeve and which extends from the end opposite the tooth-treatment implement of the handpiece sleeve as far as the zone of the tooth-treatment implement. At its commencement, the coolant line section has a radially outwardly extending inlet aperture. The known handpiece is adapted to be inserted into the open end of a drive element. The walls of the drive element possess, in the zone of this open end, at their inner side, an annular duct connected with a coolant line through which the coolant supplied passes, via the radially outwardly extending inlet aperture, into the coolant line section leading to the zone of the tooth-treatment implement.

In the inoperative condition, the handpiece is stored in a condition separate from the drive element, so that in addition to the above-mentioned danger of clogging, dust, dirt or other contaminants may pass into the inlet aperture, extending radially to the open air, of the coolant line section. Such contaminants can be once again removed only with great difficulty, so that the operational reliability of this known handpiece is greatly impaired.

In the case of a handpiece of the type mentioned at the outset, such contaminants are avoided since, instead of a radially outwardly extending inlet aperture of the coolant line section, there is provided a separate coolant duct in the walls of the handpiece sleeve having an inlet aperture facing the handpiece interior. Due to this inwardly directed, protected arrangement of the last-mentioned inlet aperture, it is avoided as indicated hereinabove-that during storage of the handpiece in the inoperative condition dust, dirt or other contaminants pass into the inlet aperture.

In the case of the dental handpiece according to FIGS. 2 and 3 of the German Offenlegungsschrift No. 23 34 448 mentioned at the outset, the coolent duct has an inlet aperture which faces outwardly in the inoperative condition, so that here again contaminants are able to pass into the inlet aperture.

It is the underlying problem of the invention to provide a dental handpiece of the type mentioned at the outset having protected arrangement of the inlet aperture of the coolant duct, wherein clogging can readily be eliminated both in the coolant duct arranged in the walls of the handpiece sleeve and also in the coolant line section extending to the tooth-treatment implement.

For the solution of this problem, according to the invention it is proposed that the coolant duct arranged in the walls of the handpiece sleeve extends substantially rectilinearly and substantially radially, the location of the releasable connection of the coolant duct with the coolant line section leading to the zone of the tooth-treatment implement being arranged in the walls of the handpiece sleeve.

Due to the substantially rectilinear extent of the coolant duct, the formation of clogging materials is made difficult from the very outset. Due to the fact that the location accessible from the exterior of the releasable connection of the coolant duct with the attached coolant line section is arranged in the walls of the handpiece sleeve, from this location outwardly through the walls of the handpiece, in extremely simple and reliable manner, both the coolant duct and also the coolant line section can be freed from clogging with the aid for example of a cleaning wire. At the same time, also simultaneously, the transition at the said location of the releasable connection is cleaned. If so required, it is also readily possible to replace the coolant line section designed for example as a flexible line.

In this connection, it is especially expedient if there is provided at the handpiece sleeve a closure member which is accessible from the exterior, which covers over the location of the releasable connection and, for the purpose of making this location accessible, is arranged to be releasable. After release of the closure member, the coolant duct and/or the coolant line section can readily be cleaned or the latter can readily be replaced. Expediently, there is provided between the closure member and the handpiece sleeve a seal sealing off the releasable connection.

The coolant line section extending to the zone of the tooth-treatment implement can be arranged, at least over a portion of its length, in the walls of the handpiece sleeve or in a longitudinal groove formed in the walls of the handpiece sleeve.

Furthermore, the handpiece sleeve may be surrounded by an external sleeve adapted to be made fast on it and which simultaneously may constitute the closure member which is accessible from the exterior. In this case, it is expedient if the outer sleeve has a radially extending inlet line bearing with its mouth at the end of the radially extending coolant duct, and connected thereto an axially extending outlet line at the debouching portion of which the coolant line section leading to the zone of the tooth-treatment implement is attached.

An expedient embodiment is characterised in that at the end of the substantially radial extent of the coolant duct there is connected a duct prolongation or extension extending substantially axially in the direction of the tooth-treatment implement and which debouches at the tool-side end of the handpiece sleeve out of the latter and is there connected with the coolant line section arranged in the outer sleeve and extending to the zone of the tooth-treatment implement.

A further embodiment consists in that the coolant line section leading to the zone of the tooth-treatment implement projects, in the direction opposite to the tool-side end of the handpiece sleeve, into an annular chamber provided within the outer sleeve and into which there is screwed as supplementary closure member an annular cover which, for receiving the end projecting into the annular chamber of the coolant line section is formed with an annular incision. With this arrangement, the end of the coolant line section projecting into the annular incision may be sealed off with a closure cover disposed releasably at the bottom of the annular incision. After screwing out the annular cover and, if appropriate, removal of the closure cover, the coolant line section extending to the zone of the tooth-treatment implement can be readily cleaned or freed from clogging by an axially introduced cleaning wire or, after pulling-out out of the receiving bore formed in the handpiece sleeve, replaced by a fresh coolant line section.

The outer sleeve mentioned can be screwed on to the handpiece sleeve or pushed on to the handpiece sleeve and secured on the latter by means of a radial screw.

A further embodiment consists in that there is releasably arranged in a recess formed in the handpiece sleeve or in a recess formed in the outer sleeve surrounding the handpiece sleeve a deflecting member constituting the closure member and having an inlet line bearing with its mouth at the outlet aperture of the radially extending coolant duct and connected thereto an axially extending outlet line at the debouching portion of which there is connected the coolant line section extending to the zone of the tooth-treatment implement. The said deflecting member may be fixed by a radial screw on the handpiece sleeve or on the outer sleeve.

In the walls of the handpiece sleeve there may be arranged a plurality of coolant ducts the inlet aperture of which facing the handpiece interior is each connected with a special coolant line for varying coolants, for example, water, air, spray.

In particular with regard to the replaceable arrangement of the coolant line section extending from the location of the releasable connection with the coolant duct to the zone of the tooth-treatment implement, an embodiment is advantageous according to which the handpiece sleeve is releasably connected with an extending sleeve extending towards the tooth-treatment implement and whereby the handpiece sleeve and the prolonging sleeve are each provided with an external longitudinal groove for receiving the coolant line section extending to the zone of the tooth-treatment implement, the prolonging sleeve engaging with one of its ends into the implement-side end of the handpiece sleeve and the two sleeves being provided in this engagement zone with locking means passing into the locking position due to mutual rotation of the two sleeves, for preventing mutual longitudinal displacement of the two sleeves, and whereby there is arranged in the handpiece sleeve a counter-nut adapted to be screwed in an internal thread of the said handpiece sleeve and which, for preventing mutual rotation of the two sleeves disposed in the said locking position, is adapted to be tightened against the end of the prolonging sleeve, the longitudinal grooves of the two sleeves extending, in the locking position, along the same generated line of the two sleeves.

After release of this so-called wrench or twist connection, i.e. after release of the above-mentioned counter-nut, and also after removal or release of the said coolant line section and optionally of the closure member, due to mutual rotation the locking means of the two sleeves can be put out of engagement, whereupon the two sleeves can be separated from each other by pulling-apart, in order that in case of need the drive shaft mounted in the prolonging sleeve can be extracted or replaced. After renewed insertion of the drive shaft into the prolonging sleeve, the latter is pushed, with its end having the locking means, into the handpiece sleeve and rotated relative to the latter, until the locking means of the two sleeves are in engagement with each other and the longitudinal grooves of the two sleeves are in the corresponding position, i.e. extend along a common generated line, whereupon the coolant line section can once again be inserted into the longitudinal grooves and releasably connected with the coolant duct.

BRIEF DESCRIPTION OF THE DRAWING

FIG. 1 shows a dental handpiece with a drive element and with releasable connection of a coolant duct arranged in the handpiece sleeve with a coolant line section extending to the zone of the tooth-treatment implement, as seen in lateral elevation, FIG. 2 shows the dental handpiece without drive element, in longitudinal section, FIG. 3 shows a section taken along the line III—III of FIG. 2, FIG. 21 shows a variant relative to FIG. 4, FIG. 22 shows a view in the direction of the arrow XXII in FIG. 21, FIG. 23 shows a further variant relative to FIG. 4, FIG. 24 shows a further variant relative to FIG. 4.

DESCRIPTION OF PREFERRED EMBODIMENTS

Figure 25:
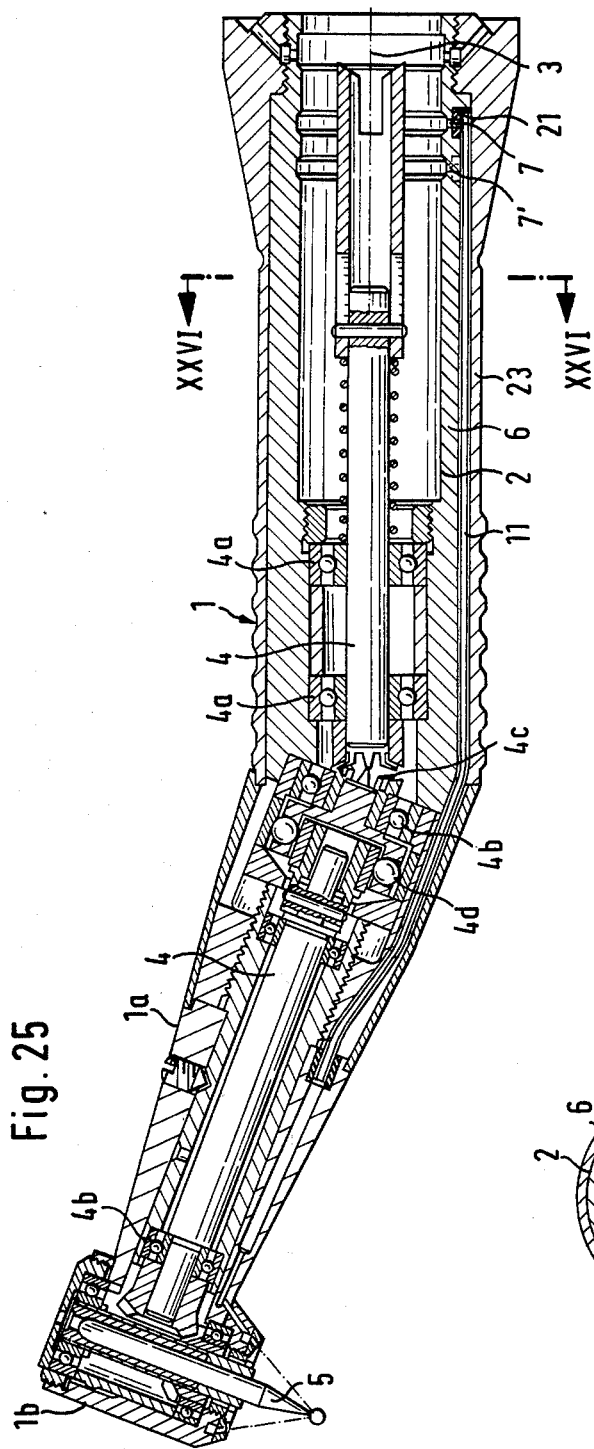
FIG. 25 shows a variant relative to FIG. 2.
Figure 26:
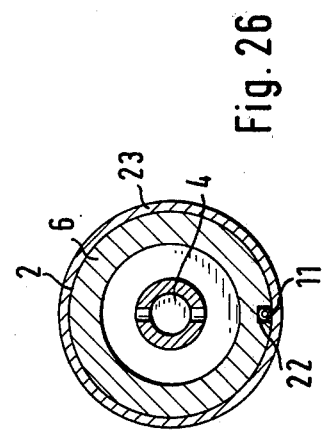
FIG. 26 shows a section taken along the line XXVI—XXVI in FIG. 25.

Referring to FIGS. 1, 2 and 25, the dental handpiece 1 comprises a cylindrical handpiece sleeve 2 in which there is mounted a drive shaft 4 extending coaxially to the shaft 3 of the handpiece sleeve 2, with the aid of the bearing 4a. In the case of the embodiment according to FIG. 25, the handpiece has an angled element 1a at one end of which there is arranged an angle head 1b. The portion of the drive shaft 4 mounted in the angled element 1a with the aid of the bearing 4b is connected via a gear-wheel system 4c and a ball-type planetary transmission system 4d with the main portion of the drive shaft 4. As is apparent from FIGS. 2 and 25, the drive shaft 4 is connected at the left-hand end with a rotatable tooth-treatment implement 5 which, according to FIG. 25, is a drill.

At the handpiece end opposite the tooth-treatment implement 5, according to FIG. 1 there is arranged a drive element 13, for example an electrical micromotor which is releasably inserted with a tubular coupling element 14 in an axial receiving aperture 15 of the handpiece sleeve 2. For releasable locking with the handpiece sleeve 2, as shown in FIG. 2, there is arranged at the drive element 13 or at the tubular coupling element 14 thereof a coupling hook 13b adapted to be loaded in the radial direction by a compression spring 13a and which engages into an annular groove 13c formed in the handpiece sleeve 2 and can be put out of engagement from the exterior, against the action of the compression spring 13a. Due to this mode of mechanical coupling, it is possible for the handpiece 1 and the drive element 13 to be rotated mutually about the longitudinal axis 3 by more than 360°.

Referring to FIG. 1, the tubular coupling element 14 has a first coolant line 8 emerging with a radial outlet aperture 16 out of the cylindrical walls of the coupling element 14. As indicated in FIG. 1 by the second outlet aperture 16', also two or more coolant lines 8 arranged in juxtaposition may be provided for feeding varying coolants, for example air and water. The coolant line 8 is supplied through an energy supply hose 17 and an end muff 19 of the drive element 13, with coolant. Arranged in the coolant line 8 is also a control member 18 having manipulating means 18a. Through the energy supply hose, also there is supplied to the drive element 13 the required energy, for example electrical current.

In the walls 6 of the handpiece sleeve 2 delimiting the axial receiving aperture 15 there is arranged a coolant duct 7 (or for example according to FIG. 2 two (or more) coolant ducts 7, 7'). The inlet aperture 9 or 9, 9', facing the handpiece interior 10, of the coolant duct 7 or 7' (FIG. 2) is connected with the outlet aperture 16 or 16' of the coolant line 8 via annular duct 9a or 9a' arranged at the inner side of the walls 6 of the handpiece sleeve 2. Thus, it is guaranteed that, in the event of the afore-mentioned mutual rotation of the handpiece 1 and the drive element 13 through 360° in any direction of rotation, coolant is able to exit from the outlet aperture 16 or 16' and pass via the annular duct 9a or 9a', through the inlet aperture 9 or 9', into the coolant duct 7 or 7' (cf. also FIGS. 13 and 18).

The coolant duct 7 or 7' is releasably connected with a second coolant line section 11 or 11' leading to the zone of the tooth-treatment implement 5 and extending substantially axially, at a location 12 which is readily accessible from the exterior.

As apparent from the drawings, the coolant duct 7 or 7' arranged in the walls 6 of the handpiece sleeve 2 extends rectilinearly and substantially radially. The location, accessible from the exterior, of the releasable connection of the coolant duct 7 or 7' with the coolant line section 11 or 11' extending to the tooth treatment implement 5 is located in the walls 6 of the handpiece sleeve 2.

Provided at the handpiece sleeve 2 is a closure member 20 which is accessible from the exterior, which covers over the said location 12 of the releasable connection and for example according to FIG. 2 is, for the rendering accessible of this location, arranged to be removable in simple manner by means of a radial screw 37. Between the closure member 20 and the handpiece sleeve 2 there is provided a seal 21 sealing off the releasable connection. As for example FIGS. 16 to 22 show, the coolant line section 11 or 11' leading to the zone of the tooth-treatment implement 5 can be arranged at least over a portion of its length in the walls 6 of the handpiece sleeve 2. Referring to FIG. 2, however, also the said coolant section 11 can, at least over a portion of its length, be arranged in an outer longitudinal groove 22 formed in the walls 6 of the handpiece sleeve 2 or in an outer longitudinal groove 51 formed in a prolonging sleeve 50 connected with the handpiece sleeve 2.

Figure 4:
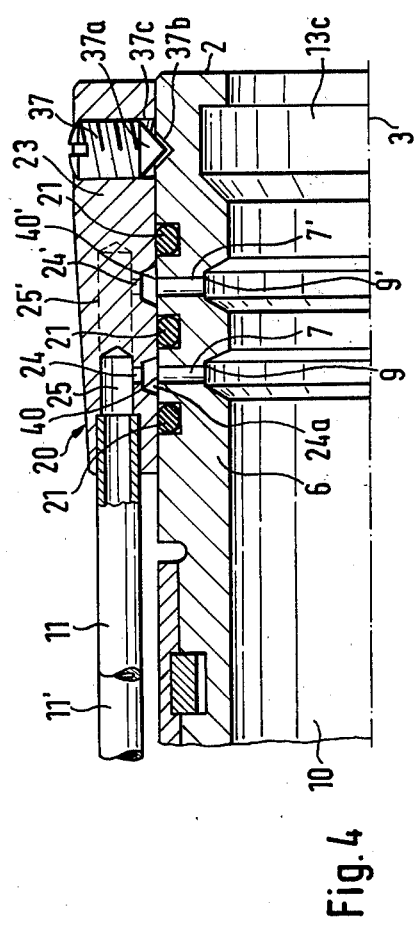
FIG. 4 shows the location of the releasable connection of the coolant duct arranged in the handpiece sleeve with the coolant line section leading to the zone of the tooth-treatment implement, drawn to a larger scale and in longitudinal section.

In the case of the embodiments according to FIGS. 5 to 10, 13 to 15, 25 and 26, the handpiece sleeve 2 is surrounded by an outer sleeve 23 adapted to be fixed on it. The outer sleeve can, with this arrangement, according to FIGS. 25 and 26 be screwed to the handpiece sleeve 2. In particular in the case of the embodiment according to FIG. 4, the outer sleeve 23 simultaneously forms the closure member 20. In the case of this embodiment, the outer sleeve 23 has a radially extending inlet line 24 bearing with its mouth at the end of the radially extending coolant duct 7 or 7' and attached thereto an axially extending outlet line 25. At the outlet portion of the outlet line 25, there is connected the coolant line section 11 or 11' extending to the zone of the tooth-treatment implement 5. The outer sleeve 23 is secured with the aid of a radial screw 37 on the handpiece sleeve 2 against rotation and longitudinal displacement. Thereby, in the case of the embodiment according to FIG. 4 the radial screw 37 engages with its apex 37a into a peripheral groove 37b of the handpiece sleeve 2, and the inlet line 24 of the outer sleeve 23 starts from an inner annular groove 24a, so that the outer sleeve 23 can be put into or secured in any optional rotational position on the handpiece sleeve 2.

Figure 5:
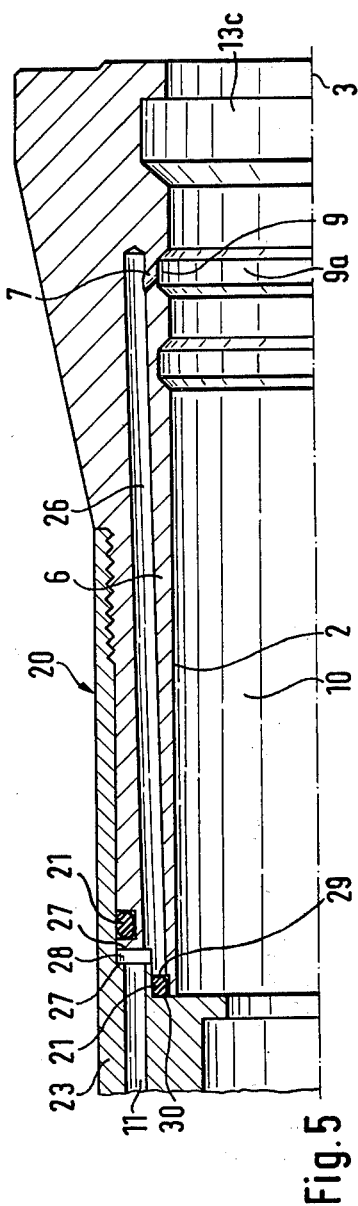
FIG. 5 shows a variant relative to FIG. 4.
Figure 8:
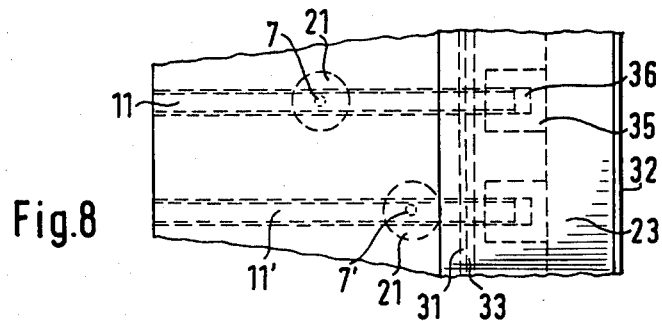
FIG. 8 shows a view in the direction of the arrow VIII in FIG. 6.
Figure 7:
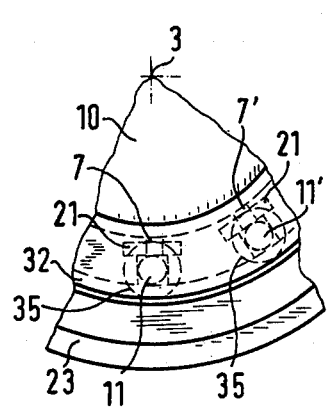
FIG. 7 shows a view in the direction of the arrow VII in FIG. 6.
Figure 6:
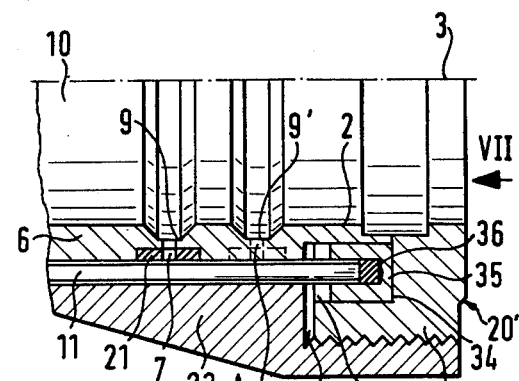
FIG. 6 shows a further variant relative to FIG. 4.
Figure 10:
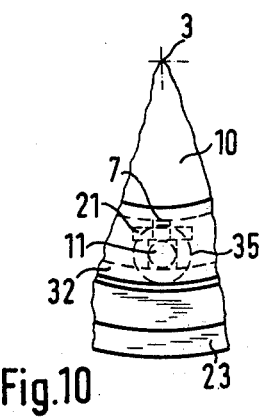
FIG. 10 shows a view in the direction of arrow X in FIG. 9.
Figure 9:
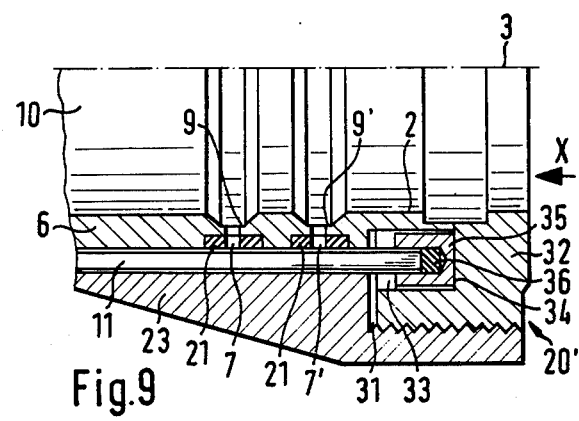
FIG. 9 shows a variant relative to FIG. 6.
Figure 11:
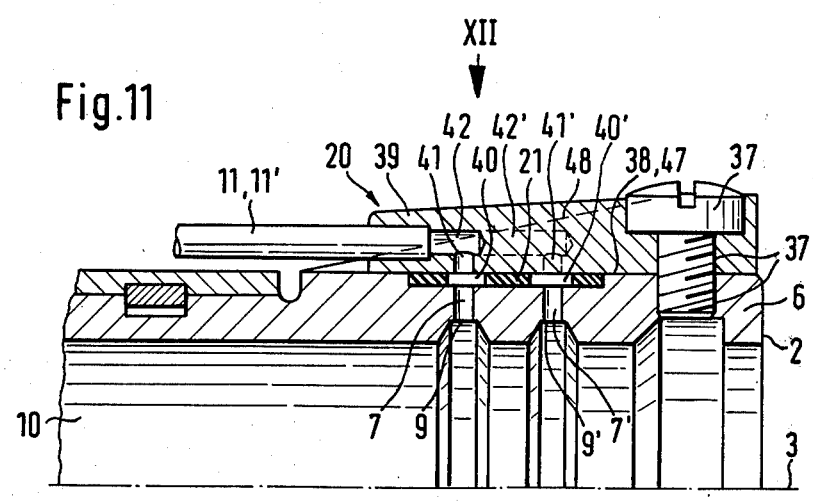
FIG. 11 shows a further variant relative to FIG. 4.
Figure 12:
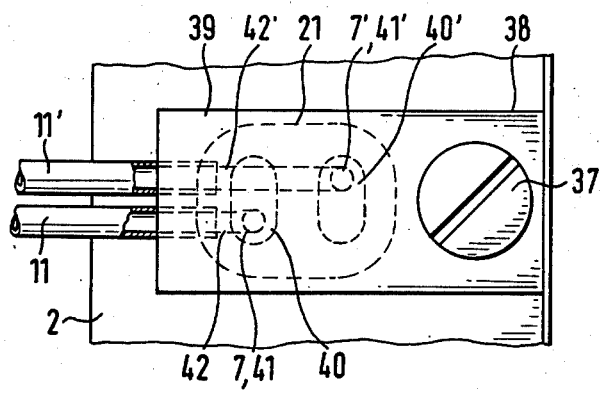
FIG. 12 shows a view in the direction of the arrow XII in FIG. 11.

Referring to FIG. 5, there is provided at the radially outer end of the coolant duct 7, a duct prolongation 26 attached in the walls of the handpiece sleeve 2 to extend substantially axially in the direction to the tooth-treatment implement 5. The duct prolongation 26 terminates at the tool-side end of the handpiece sleeve 2 and is there connected with the coolant line section 11 arranged in the outer sleeve 23 and extending to the zone of the tool 5. This connection comprises an annular groove 28 formed by spaced end wall annular faces 27 of the handpiece sleeve 2 and the outer sleeve 23. The duct prolongation 26 and the coolant line section 11 are arranged radially offset to each other. In the vicinity of the portion directed into the annular groove 28, the duct prolongation 26 has an axial outlet aperture 29 sealed-off by a sealing ring constituting the seal 21 and arranged between two further end wall annular faces 30 of the handpiece sleeve 2 and the outer sleeve 23. Arranged on the side opposite the coolant line section 11 of the annular groove 28, between the outer wall of the handpiece sleeve 2 and the inner wall of the outer sleeve 23, is a further sealing ring constituting the seal 21. The two said sealing rings may be constituted by O-rings. The arrangement of the annular groove 28 and of the said sealing rings makes it possible for the handpiece sleeve 2 and the outer sleeve 23 to be screwed together and secured in any optional rotational position relative to each other, whereby the flow of coolant from the duct prolongation 26 to the coolant line section 11 is guaranteed by the said annular groove 28.

In the case of the embodiments according to FIGS. 6 to 10, the coolant line section 11 extending to the zone of the implement 5 projects, in the direction opposite to the implement-side end of the handpiece sleeve 2, into an annular chamber 31 provided within the outer sleeve 23 and open in the radial direction. Screwed into the annular chamber 31, as a supplementary closure member 20' is an annular cover 32 formed with an annular incision 33 for receiving the end of the coolant line section 11 projecting into the annular chamber 31. The end of the coolant line section 11 projecting into the annular incision 33 is releasably sealed off with a closure cover 35 bearing at the bottom 34 of the annular incision 33. Between the closure cover 35 and the end of the coolant line section 11 is a cover 36. The seal 21 comprises, as for example also in the case of the embodiments according to FIGS. 2, 11, 12, 23 and 24, sealing discs.

Figure 13:
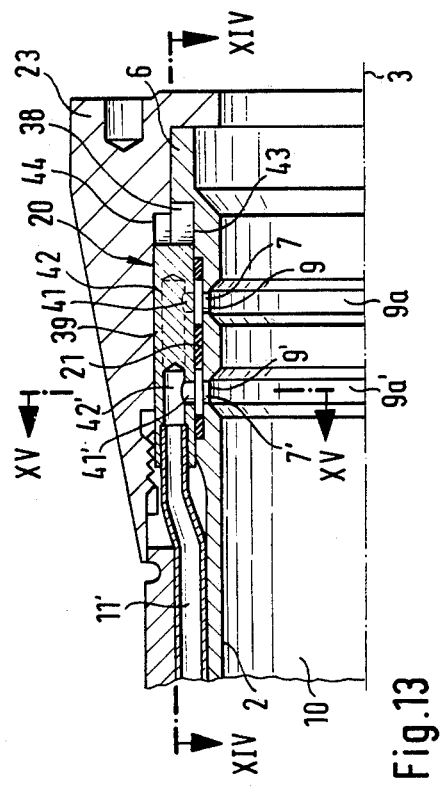
FIG. 13 shows a further variant relative to FIG. 4.
Figure 14:
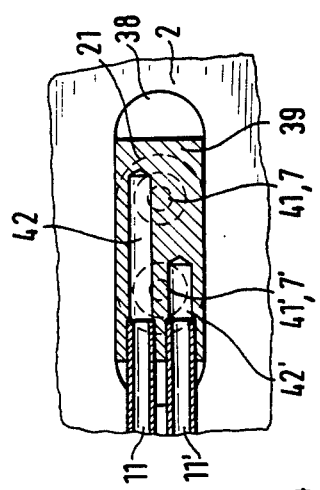
FIG. 14 shows a section taken along the line XIV—XIV in FIG. 13.
Figure 15:
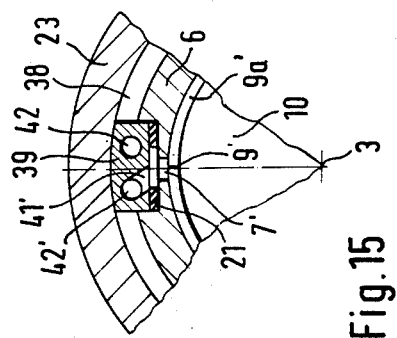
FIG. 15 shows a section taken along the line XV—XV in FIG. 13.
Figure 17:
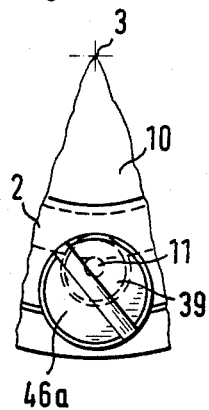
FIG. 17 shows a view in the direction of the arrow XVII in FIG. 16.

In the case of the embodiments according to FIGS. 1, 2, 3 and 11 to 24, there is releasably arranged in a recess 38 of the handpiece sleeve 2 a deflecting member 39 constituting the closure member 20 and having an inlet line 41 bearing with its mouth at the outlet aperture 40 of the radially extending coolant duct 7 or 7' and, connected therewith, an axially extending outlet line 42 to the outlet portion of which there is connected to coolant line section 11 extending to the zone of the tooth-treatment implement 5 or which merges into the coolant line section 11 and is in one piece therewith, for example according to FIGS. 6, 9, 18 and 21. The deflecting member 39 can also be arranged in a recess formed in the outer sleeve 23 surrounding the handpiece sleeve 2. Referring to FIGS. 13 to 15, there is arranged, opposite each other in each particular instance, in the outer walls of the handpiece sleeve 2 and in the inner walls of the outer sleeve 23 a recess 43 or 44. In the chamber-like recess 38 formed in this manner, there is provided the deflecting member 39.

Referring to FIGS. 16 to 22, the recess 38 is designed as a substantially axial bore 45. Fundamentally, the recess 38 may also be designed as a radial bore. Referring to FIGS. 16 to 22, the substantially axial bore 45 extends from the end opposite the implement-side end of the handpiece sleeve 2 into the walls of the latter, there being arranged in the cylindrical recess 38 the deflecting member 39 which is also of cylindrical design. The deflecting member 39 is retained by a screwing system 46 releasably at the substantially axial bore 45. For this purpose, a sealing screw 46a is screwed from the exterior at the end face into the axial bore 45.

Figure 16:
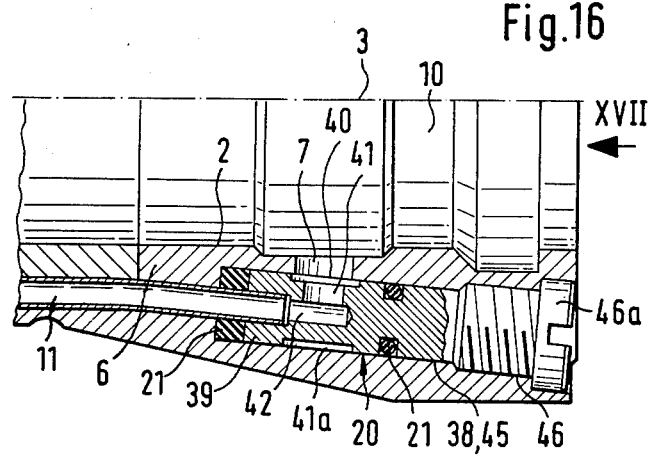
FIG. 16 shows a further variant relative to FIG. 4.
Figure 20:
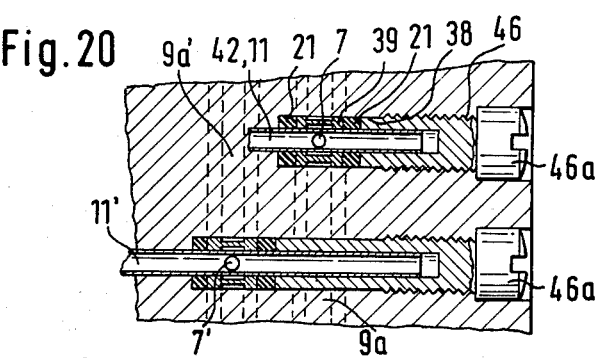
FIG. 20 shows a section located in a plane curved to correspond to the line XX—XX of FIG. 19, taken along the line XX—XX in FIG. 18.
Figure 19:
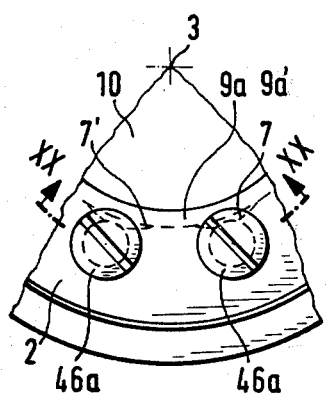
FIG. 19 shows a view in the direction of the arrow XIX in FIG. 18.
Figure 18:
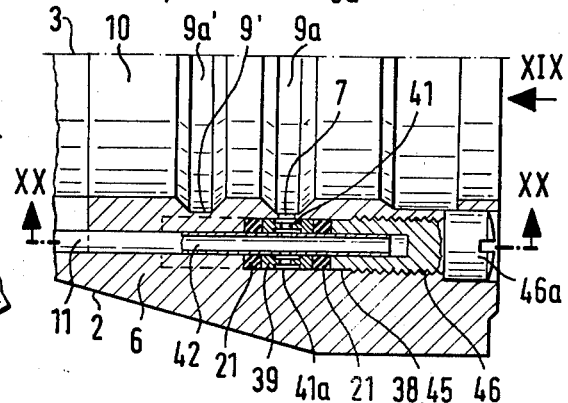
FIG. 18 shows a further variant relative to FIG. 4.

As apparent for example from FIGS. 16 and 18, the cylindrically designed deflecting member 39 has an annular duct 41a extending about the periphery and into which the inlet line 41 and also the coolant duct 7 or 7' terminates with its outlet aperture 40. Thus, the cylindrically formed deflecting member 39 can, without maintaining a pre-determined rotational position, be inserted into the axial bore 45 which is also cylindrical.

Referring to FIGS. 11, 12, 23 and 24, the recess 38 is designed as a depression 47 arranged in the outer walls 48 of the handpiece sleeve 2 and into which the deflecting member 39, designed as a flat member, is inserted. The deflecting member 39 can be secured to the coolant line section 11 extending to the zone of the tooth-treatment implement 5 and which for its part is releasably connected with the handpiece sleeve 2. The deflecting member 39, designed as a flat body, is adapted to be secured in pre-determined rotary position on the handpiece sleeve 2 by means of a radial screw 37 screwed into a radial tapped bore 37c of the handpiece sleeve 2. In this pre-determined rotary position, according to FIG. 24 the coolant duct 7 or 7' of the handpiece sleeve 2 and the inlet line 41 or 41' of the deflecting member 39 are in alignment.

Apart from the embodiment according to FIG. 2, also in the case of those according to FIGS. 4, 6 to 15 and 18 to 25, there are arranged in the walls 6 of the handpiece sleeve 2 a plurality of (in the case illustrated two) coolant ducts 7, 7'. The inlet aperture 9, 9' facing the handpiece interior 10 of the coolant ducts 7, 7' is in each particular instance connected with a special coolant line 8 for various coolants, for example, water, air, spray. Referring to FIG. 1, only one such coolant line 8 is visible, although located rearwardly thereof there is provided a further coolant line with the illustrated radial outlet aperture 16'.

Referring to FIGS. 1, 2, 4, 6 to 8, 11 to 15, 18 to 20 and 24, each coolant duct 7, 7' is connected with a special coolant line section 11, 11' extending to the zone of the tooth-treatment implement 5. According to FIGS. 1, 2, 4, 6 to 8, 11 to 15 and 18 and 20, these special coolant line sections 11, 11' are arranged in side-by-side relationship and according to FIG. 24, concentrically one within the other. Thus, mixing of the varying coolants is effected during emergence out of the coolant line sections 11, 11' in the zone of the tooth-treatment implement 5.

The coolant ducts 7, 7' can, however, also for the purpose of previous mixing of the varying coolants according to FIGS. 9, 10, 21 to 23 and 25, be connected with a common coolant line section 11 extending to the zone of the tooth-treatment implement 5. With this arrangement, the common coolant line section 11 serves as mixing chamber. Referring to FIG. 23, however, also at the outlet portion of the coolant ducts 7, 7' in the outlet line 42 arranged upstream of the coolant line section 11, there may be provided a special mixing chamber 49 simultaneously constituting the inlet line of the deflecting member 39.

As for example FIGS. 4, 11, 12, 13, 14, 23 and 24 show, the coolant line section 11 or 11' may be inserted (i.e. firmly or releasably) with its end facing the deflecting member 39 in a widening bore formed in the outlet line 25, 25' of the outer sleeve 23 or 42, 42' of the deflecting member 39. In the case of the fixed arrangement, in the event of clogging of the coolant line section 11 or 11', the latter can be replaced together with the deflecting member 39, with which arrangement after removal of the deflecting member 39, for example subsequent to previous release of the radial screw 37, the coolant duct 7 or 7' can readily be cleaned.

Just such replacement of the deflecting member 39 with the seals 21 and together with the coolant line section 11 or 11' thereof is possible also in the case of the embodiments according to FIGS. 16 to 22, i.e. after previous release and drawing-out of the sealing screw 46a, in particular if the latter is connected with the deflecting member 39 and the seals 21.

The deflecting member 39 having two or more coolant line sections 11, 11', for example according to FIG. 24, can quite readily be replaced by a deflecting member 39 having fewer, for example only one coolant line sections 11, if for example there is employed a drive element 13 having only one coolant line 8. In this manner, simple re-equipment of the dental handpiece is possible.

In the drawings, the apertures, lines, etc. associated with or connected sequentially of the second coolant duct 7' are designated with a numeral having a stroke, to correspond to the numerals of the corresponding elements of the coolant duct 7.

In the case of the embodiment according to FIG. 2, the handpiece sleeve 2 is releasably connected with a prolonging sleeve 50 extending to the tooth-treatment implement 5. Both the handpiece sleeve 2 and also the prolonging sleeve 50 are in each instance formed with an external longitudinal groove 22, 51 for receiving the coolant line section 11, 11' extending to the zone of the tooth-treatment implement 5. With this arrangement, there is provided on the prolonging sleeve 50 a cover sleeve 57 secured by a radial retaining screw 59 to an inner sleeve 58 rotatable relative to the drive shaft 4. Arranged at the tool-side end of the handpiece 1 is also an end sleeve 60 on the prolonging sleeve 50. The prolonging sleeve 50 engages with its right-hand end in FIG. 2 into the tool-side end of the handpiece sleeve 2. The two sleeves 2, 50 are provided in this engagement zone with locking means 52, 53 adapted to be put into the locking position by mutual rotation of the two sleeves and which, in the locking position, prevent mutual longitudinal displacement of the two sleeves 2, 50. Arranged in the handpiece sleeve 2 is a lock-nut 55 adapted to be screwed into an internal screwthread 54 of the sleeve and which, for preventing mutual rotation of the two sleeves 2, 50 disposed in the said locking position is adapted to be screwed to securement against the end of the prolonging sleeve 50. This securement is effected when the longitudinal grooves 22, 51, after appropriate rotation of the two sleeves, extend along a common generated line of the two sleeves 2, 50, and the locking means 52, 53 are in engagement.

For forming the locking means 52, 53, the engaging end of the prolonging sleeve 50 according to FIG. 3 is provided with external flattened portions 50a distributed about the periphery, so that in the zone of these flats 50a there is a hexagonal cross-section with rounded corners of the prolonging sleeve 50. In these rounded transition zones of the flats 50, there are arranged radial grooves extending in the peripheral direction and which, due to mutual rotation of the two sleeves 2, 50, pass into engagement with corresponding inner radial ribs on the handpiece sleeve 2. The said radial grooves and radial ribs constitute the locking means 52, 53.

As apparent from FIG. 2, the lock-nut 55 is provided with two aperture-like or incision-like deformations 56 for engagement with the engagement means of a key (not shown).

Lock nut 55 has key surfaces 56, i.e., slots which during the assembly of the instrument engage an associated key. This key cannot be shown in the assembled state of the handpiece in FIG. 2 of the drawing. The screwdriver-like key with frontal key areas may be inserted from behind through the handpiece interior till it contacts the key areas 56 of the lock nut 55. It is understood that the key must be hollow on the inside in order to be inserted over the shaft.

Several similar annular grooves 52, 53 on sleeves 50 and 2 are interrupted by flattened portions 50a on sleeves 50 and 2 and thus can engage in the manner of a bayonet catch. Staggered annular grooves may thus be engaged (similar to a thread) and thus interlock the two sleeves in the axial direction. By the bayonet-like engagement of elements 52, 53, 50a of sleeves 50 and 2, these two sleeves become positively connected. The axial tension force is produced by turning the lock nut 55. The toolside frontal area of the lock nut 55 is axially tension-locked to sleeve 50 via the ball bearing outside race of bearing 4a.

We claim:

1. A dental handpiece comprising: a handpiece sleeve; a drive shaft extending axially of said sleeve and connectable in use to a dental instrument at one end of the handpiece to drive the instrument; a first coolant supply line provided for the handpiece; a coolant duct provided in the wall of said sleeve and communicating at an inner end with said first coolant supply line, said inner end being located to face the interior of the sleeve; and a second coolant supply line communicating with an opposite outer end of said coolant duct and extending towards said one end of the handpiece; said coolant duct being a generally rectilinear duct extending generally radially between said inner and said outer end of the duct; said second coolant supply line being releasably connected to said outer end of the coolant duct at a location in the wall of said handpiece sleeve which permits manipulation externally of the handpiece to connect together and to release the connection between said second coolant supply line and said outer end of the coolant duct; and a closure member at the handpiece sleeve which is accessible from the exterior and which covers-over said location of the releasable connection, said closure member being arranged to be releasable for making said location accessible; the handpiece sleeve being surrounded by an outer sleeve adapted to be fixed upon it; the second coolant line having a portion projecting in a direction away from the instrument end of the handpiece sleeve into an annular chamber provided within the outer sleeve and into which, as a supplementary closure member, there is screwed an annular cover having an annular socket for receiving the projecting end of the second coolant line.

2. A dental handpiece according to claim 1, including a seal positioned between the closure member and the handpiece sleeve for sealing-off the releasable connection.

3. A dental handpiece according to claim 1, in which the second coolant line is arranged, at least over a portion of its length, in the wall of the handpiece sleeve.

4. A dental handpiece according to claim 3, in which the second coolant line is arranged, at least over a portion of its length, in a longitudinal groove formed in the wall of the handpiece sleeve.

5. A dental handpiece according to claim 1, in which the outer sleeve constitutes said closure member.

6. A dental handpiece according to claim 5, in which the outer sleeve has a radially extending inlet line communicating at its inner end with the outer end of the coolant duct and adjacent thereto an axially extending outlet line having an outlet which communicates with said second coolant line.

7. A dental handpiece according to claim 1, wherein the projecting end of the second coolant line is releasably sealed with a closure cover in contact with a bottom of the annular socket.

8. A dental handpiece according to claim 7, in which a seal is provided between the closure cover and the projecting end of the second coolant line.

9. A dental handpiece according to claim 1, in which said outer sleeve is screwed-on to the handpiece sleeve.

10. A dental handpiece according to claim 1, in which said outer sleeve is pushed-on to the handpiece sleeve and is secured on the latter by means of a radial screw.

11. A dental handpiece according to claim 1, including a recess in the handpiece sleeve in which there is releasably arranged a deflecting member constituting said closure member,
said deflecting member having an inlet line bearing with its mouth at the outer end of said coolant duct, and an axially extending outlet line with an outlet connected to the second coolant line.

12. A dental handpiece according to claim 1, including a plurality of radially coolant ducts arranged in the wall of the handpiece sleeve, inner ends of the ducts each being connected to a respective first coolant line associated with a predetermined coolant such as water, air, or spray.

13. A dental handpiece according to claim 12, in which each coolant duct is also connected to a respective second coolant line.

14. A dental handpiece according to claim 13, in which the second coolant lines are arranged coaxially within each other.

15. A dental handpiece according to claim 12, in which the coolant ducts are connected with a common second coolant line in which the coolants corresponding to the coolant ducts can be mixed.

16. A dental handpiece according to claim 15, in which a mixing chamber is arranged intermediate the coolant ducts and the common second coolant line.

17. A dental handpiece according to claim 1, in which the handpiece sleeve includes a prolonging sleeve releasably connected thereto and extending to a zone at which the dental instrument can be mounted, the handpiece sleeve and the prolonging sleeve being each provided with a respective external longitudinal groove which receives the second coolant line, and the prolonging sleeve engaging with one of its ends into one end of the handpiece sleeve and the two sleeves in this engagement zone being provided with locking means passing into a locking position due to mutual rotation of the two sleeves, for preventing mutual longitudinal displacement of the two sleeves, and in which there is arranged in the handpiece sleeve a lock-nut adapted to be screwed into an internal screwthread formed in the latter, said lock-nut being adapted to be tightened, for preventing mutual rotation of the two sleeves disposed in the said locking position against the end of the prolonging sleeve, and the longitudinal grooves of the two sleeves extending, in the locking position, along the same generated line of the two sleeves.

18. A dental handpiece according to claim 17, in which, for forming the locking means, the engaging end of the prolonging sleeve is provided with external flats distributed about the periphery and in the zones of transition of which there are provided radial grooves extending in the peripheral direction and which are adapted to be put into engagement by mutual rotation of the sleeves with corresponding inner radial ribs on the handpiece sleeve.

19. A dental handpiece according to claim 17, in which the lock-nut is provided at least at one end face with deformations for engagement with the engagement means of a key.

20. A dental handpiece according to claim 3, wherein the second coolant line is arranged at least partly in said outer sleeve; and an axial duct prolongation extending in the wall of the handpiece sleeve and having an outlet at the instrument end of the handpiece sleeve which communicates with the second coolant line; said duct prolongation and the second coolant line being connected with each other via an annular groove formed by spaced end wall annular faces of said handpiece sleeve and said outer sleeve; said duct prolongation and said second coolant line being arranged radially offset relative to each other; said duct prolongation having, in the vicinity of the outlet directed into the annular groove, an axial outlet aperture.

21. A dental handpiece according to claim 20, wherein said axial outlet aperture is sealed off by a first sealing ring arranged between two further end wall annular faces of said handpiece sleeve and said outer sleeve; and a second sealing ring being arranged on a side of said annular groove opposite said second coolant line between an outer wall of said handpiece sleeve and an inner wall of said handpiece sleeve.

22. A dental handpiece comprising: a handpiece sleeve; a drive shaft extending axially of said sleeve and connectable in use to a dental instrument at one end of the handpiece to drive the instrument; a first coolant supply line provided for the handpiece; a coolant duct provided in the wall of said sleeve and communicating at an inner end with said first coolant supply line, said inner end being located to face the interior of the sleeve; and a second coolant supply line communicating with an opposite outer end of said coolant duct and extending towards said one end of the handpiece; said coolant duct being a generally rectilinear duct extending generally radially between said inner and said outer end of the duct; said second coolant supply line being releasably connected to said outer end of the coolant duct at a location in the wall of said handpiece sleeve which permits manipulation externally of the handpiece to connect together and to release the connection between said second coolant supply line and said outer end of the coolant duct; a closure member at the handpiece sleeve which is accessible from the exterior and which covers-over said location of the releasable connection, said closure member being arranged to be releasable for making said location accessible; a recess in the handpiece sleeve in which there is releasably arranged a deflecting member constituting said closure member, said deflecting member having an inlet line bearing with its mouth at the outer end of said coolant duct, and an axially extending outlet line with an outlet connected to the second coolant line; the deflecting member being arranged in a recess formed in an outer sleeve surrounding the handpiece sleeve.

23. A dental handpiece according to claim 22, in which there is arranged a corresponding recess in the outer wall of the handpiece sleeve and in the inner wall of the outer sleeve, located opposite each other, said recesses forming a chamberlike recess in which the deflecting member is arranged.

24. A dental handpiece according to claim 22, in which said recess is designed as a depression arranged in the outer wall of the handpiece sleeve or the outer sleeve, into which is inserted the deflecting member, designed as a flat member.

25. A dental handpiece according to claim 22, in which the deflecting member is secured to the second coolant line, said second coolant line being arranged to be releasable at the handpiece sleeve.

26. A dental handpiece comprising: a handpiece sleeve; a drive shaft extending axially of said sleeve and connectable in use to a dental instrument at one end of the handpiece to drive the instrument; a first coolant supply line provided for the handpiece; a coolant duct provided in the wall of said sleeve and communicating at an inner end with said first coolant supply line, said inner end being located to face the interior of the sleeve; and a second coolant supply line communicating with an opposite outer end of said coolant duct and extending towards said one end of the handpiece; said coolant duct being a generally rectilinear duct extending generally radially between said inner and said outer end of the duct; said second coolant supply line being releasably connected to said outer end of the coolant duct at a location in the wall of said handpiece sleeve which permits manipulation externally of the handpiece to connect together and to release the connection between said second coolant supply line and said outer end of the coolant duct; a closure member at the handpiece sleeve which is accessible from the exterior and which covers-over said location of the releasable connection, said closure member being arranged to be releasable for making said location accessible; a recess in the handpiece sleeve in which there is releasably arranged a deflecting member constituting said closure member, said deflecting member having an inlet line bearing with its mouth at the outer end of said coolant duct, and an axially extending outlet line with an outlet connected to the second coolant line; said recess being designed as a substantially axial bore extending from the end of the handpiece sleeve into the wall of the handpiece sleeve, and the deflecting member being a cylindrical member received in said bore.

27. A dental handpiece according to claim 26, in which the cylindrical member is releasably retained by a screw in the substantially axial bore.

* * * * *